United States Patent
Zhang et al.

(10) Patent No.: US 10,881,309 B2
(45) Date of Patent: Jan. 5, 2021

(54) PPG MEASUREMENT OF ARTERIAL HEALTH USING DISEASE LIBRARY

(75) Inventors: Michael Zhang, Winnipeg (CA); Zhaopeng Fan, Winnipeg (CA); Marshall Ring, Winnipeg (CA); Sara Korosch, Winnipeg (CA); David Keenan, Winnipeg (CA); Gerald Lefevre, Winnipeg (CA)

(73) Assignee: Arterial Stiffness Inc., Winnipeg (CA)

( * ) Notice: Subject to any disclaimer, the term of this patent is extended or adjusted under 35 U.S.C. 154(b) by 634 days.

(21) Appl. No.: 13/825,225

(22) PCT Filed: Sep. 20, 2011

(86) PCT No.: PCT/CA2011/050577
§ 371 (c)(1),
(2), (4) Date: Oct. 3, 2017

(87) PCT Pub. No.: WO2012/037679
PCT Pub. Date: Mar. 29, 2012

(65) Prior Publication Data
US 2018/0146869 A1    May 31, 2018

Related U.S. Application Data

(60) Provisional application No. 61/384,437, filed on Sep. 20, 2010.

(51) Int. Cl.
*A61B 5/024* (2006.01)
*A61B 5/02* (2006.01)
(Continued)

(52) U.S. Cl.
CPC ...... *A61B 5/02416* (2013.01); *A61B 5/02007* (2013.01); *A61B 5/1455* (2013.01);
(Continued)

(58) Field of Classification Search
None
See application file for complete search history.

(56) References Cited

U.S. PATENT DOCUMENTS 6,322,515 B1    11/2001  Goor et al.
2006/0009700 A1*  1/2006  Brumfield ............ A61B 5/0261
                                                    600/504
(Continued)

FOREIGN PATENT DOCUMENTS

EP          2191771        6/2010

OTHER PUBLICATIONS

Breakthrough in Clinical Cardiology: In-Office Assessment with Pulse Wave Velocity (PWV) and Digital Pulse Analysis (DPA); Brian Scott Peskin et al; Townsend Letter May 2010.

*Primary Examiner* — Matthew Kremer
(74) *Attorney, Agent, or Firm* — Michael R Williams; Ryan W. Dupuis; Ade & Company Inc.

(57) ABSTRACT

The arterial health of an individual can be determined by: attaching a fingertip photopiethysmography device to a fingertip of the hand of the elevated arm of the individual; measuring the analog pulse contour of the individual using the fingertip photopiethysmography device; digitizing the analog pulse contour; analyzing the digitized pulse contour for stable waveforms; processing the stable waveforms of the digitized pulse contour using dynamic time warping; comparing the stable waveforms to a library of known disease state waveforms; and assigning a most probable disease state for the individual based on said comparison.

6 Claims, 2 Drawing Sheets

Normal arterial pulsation wave form.
SI=H/T (units in meters/sec)
RI=(b/a)X100%

(51) Int. Cl.
*A61B 5/1455* (2006.01)
*A61B 5/00* (2006.01)
*G16H 50/20* (2018.01)

(52) U.S. Cl.
CPC .......... *A61B 5/6826* (2013.01); *A61B 5/7264* (2013.01); *G16H 50/20* (2018.01)

(56) References Cited

U.S. PATENT DOCUMENTS

| | | | | |
|---|---|---|---|---|
| 2006/0149330 | A1* | 7/2006 | Mann | A61B 5/0031 607/34 |
| 2006/0224073 | A1* | 10/2006 | Lin | A61B 5/02007 600/513 |
| 2007/0027382 | A1* | 2/2007 | Berman | A61B 5/02028 600/347 |
| 2008/0294019 | A1* | 11/2008 | Tran | A61B 5/0006 600/301 |
| 2009/0030292 | A1* | 1/2009 | Bartnik | A61B 5/02028 600/301 |
| 2009/0234202 | A1* | 9/2009 | Goix | A61B 5/412 600/301 |
| 2009/0326349 | A1* | 12/2009 | McGonigle | A61B 5/726 600/323 |
| 2010/0228138 | A1* | 9/2010 | Chen | A61B 5/0452 600/509 |
| 2010/0292586 | A1* | 11/2010 | Rooke | A61B 5/0002 600/492 |
| 2011/0071376 | A1* | 3/2011 | McKenna | G06K 9/00557 600/336 |

* cited by examiner

Normal arterial pulsation wave form.

SI=H/T (units in meters/sec)
RI=(b/a)X100%

PPG MEASUREMENT OF ARTERIAL HEALTH USING DISEASE LIBRARY

PRIOR APPLICATION INFORMATION

The instant application is a 371 of PCT Application CA2011/050577, filed Sep. 20, 2011, now abandoned, which claimed the benefit of U.S. Provisional Patent Application 61/384,437, filed Sep. 20, 2010.

BACKGROUND OF THE INVENTION

Fingertip Photoplethysmography (PPG) is a technique that has been used for many years. In PPG, one transmits light through the fingertip, monitors the transmitted power, and relates the rise and fall of the transmitted power to the health of the patient. The contour, or shape, of the pulse indicates the health of the cardiac and arterial systems of the patient. This type of system has been reviewed and discussed in many publications, including: "Pulse Wave Analysis", M F O'Rourke and D E Gallagher, J. Hypertension 1996 vol. 14 (supplement 5), pp S147-S157; "Arterial Stiffness and Pulse Contour Analysis: an age old concept revisited", J R Cockcroft and I B Wilkinson, Clinical Science (2002) 103, 379-380; "Determination of age-related increases in large artery stiffness by digital pulse contour analysis", S C Millasseau, R P Kelly, J M Ritter and P J Chowienczyk, Clinical Science (2002, 371-377. This paper indicates that the stiffness index can be calculated from the patient height and the distance between two points on the pulse contour curve. A review in 2007 entitled "Photoplethysmography and its application in clinical physiological measurement", J. Allen, Physiological Measurement, 28 (2007) R1-R39 discusses the various applications of this technique. This review indicates that the faster paced pulse contour is coupled to a more slowly varying baseline movement, and it indicates that there is general acceptance that the PPG signal provides valuable information about cardiovascular health. The review indicates that ears, fingers and toes can be used as measurement points. This review does not mention the concept of disease library of curves.

Automated methods of PPG contour classification have been discussed in "Artificial Neural Networks (ANN) Approach to PPG Signal Classification", M. Soltane, M. Ismail, Z. A. A. Rashid, Int. J. Comp. Info. Sciences, Vol 2(1) April 2004, p 58-65, and in "Multivariate classification of systemic vascular resistance using photoplethysmography", Qim Y Lee[1], Gregory S H Chan[1], Stephen J Redmond[2], Paul M Middleton[1,3], Elizabeth Steel[4], Philip Malouf[4], Christopher Critoph[4], Gordon Flynn[4], Emma O'Lone[4] and Nigel H Lovell, 2011 *Physiol. Meas.* 32 1117. There have been various studies on the use of Dynamic Time Warping (DTW) for medical signals, including "Electrocardiagram data mining based on frame classification by dynamic time warping matching", G. Zhang, W. Kinsner and B. Huang, Comp. Methods in Biomech. and Biomed. Engineering, iFirst Article, 2009, p 1-7.

Use of PPG for monitoring patients via cellular phone have been discussed by Development of Heart Rate Monitoring for Mobile Telemedicine using Smartphone Hun Shim, Jung Hoon Lee, Sung Oh Hwang, Hyung Ro Yoon and Young Ro Yoon 13th Int. Conf. Biomedical Engineering, 2009, vol 23, Track 3, 1116-1119. In this system, a rules-based algorithm was used for classification, with a healthcare database server offering retrospective assessment of the patient information.

More recently, "The Investigation of the Effect of Aging through Photoplethysmogram Signal Analysis of Erectile Dysfunction Subjects Y. K. QAWQZEH, M. B. I. REAZ, O. MASKON, KALAIVANI CHELLAPPAN, M. T. ISLAM, M. A. M. ALI; Recent Researches in Telecommunications, Informatics, Electronics and Signal Processing, pp. 53-58 discusses an additional number which indicates a characteristic of the pulse shape, a reflection index, which is the ratio of the two peak heights found within a pulse contour. Finding the location of the peaks can be difficult for older patients, because the dichrotic notch is almost non-existent, and so the first and second derivative of the pulse contour may need to be calculated, as discussed in this paper. It has been possible in the literature to discuss characteristic pulse contour shapes and to associate these shapes with various ages and disease states of the patients, as has been shown in "The Pulse Wave Velocity as an Early Indicator of Atherosclerosis in Diabetic Subjects", G. L. WOOLAM, P. L. SCHNUR, C. VALLBONA and H. E. HOFF, *Circulation* 1962, 25:533-539. In this case, a characteristic contour was discussed as indicating diabetic issues.

In all of the above work, the measurement of pulse contour has been shown, the idea of using characteristic curves for different disease states has been discussed and the automated assessment of disease curves using classification methods has been done. A difficulty of using pulse contour shape as an indicator of disease states is that the knowledge of the person or program assessing the shape must be quite extensive. This problem becomes even more difficult if the number of characteristic shape patterns begins to increase or change with time. For example, if there are five characteristics contours that indicate five different disease states, it would be useful to have a classification method that can be automated so that the human evaluation process can be aided by automated methods. In addition, as more disease states and more characteristic contours are added to the disease library, the automated support for the human contour assessor becomes even more important. It is also possible to imagine that the pulse contour measurement process becomes quite simple, whereas the evaluation of the contours that are measured become more complex. For example, if one wishes to develop a home-based pulse contour analysis method, it would be useful to have an automated system that can run on a home computer, laptop, cellphone, or other digital device, which would allow automated evaluation of the pulse contour. This type of automated contour analysis system requires a method of characterizing the fit or closeness between the measured pulse contour of the patient and the various characteristic curves that are used in the disease library. This method should allow easy updating and transfer of information over the various network links. As well, it would be useful to allow the disease library to be updated over time as new characteristic curves are identified. This update process would be useful for insurance companies, for example, if they update the disease library for their assessors remotely via the internet.

However, no one has used DTW methods to provide the disease library and pulse contour characterization.

SUMMARY OF THE INVENTION

According to a first aspect of the invention, there is provided a method of assessing the arterial health of an individual comprises:
  a) positioning one arm of the patient such that the arm is at approximately the same height as the heart of the individual;

b) attaching a fingertip photoplethysmography device to a fingertip of the hand of said arm of the individual;

c) measuring the analog pulse contour of the individual using the fingertip photoplethysmography device;

d) digitizing the analog pulse contour;

e) analyzing the digitized pulse contour for stable waveforms;

f) processing the stable waveforms of the digitized pulse contour using dynamic time warping;

g) comparing the stable waveforms to a library of known disease state waveforms; and h) assigning a most probable disease state for the individual based on said comparison.

According to another embodiment of the invention, there is provided a method of generating a library of waveforms from individuals having a known arterial disease comprises:

a) positioning one arm of an individual having a known arterial disease such that the arm is at approximately the same height as the heart of the individual;

b) attaching a fingertip photoplethysmography device to a fingertip of the hand of said arm of the individual;

c) measuring the analog pulse contour of the individual using the fingertip photoplethysmography device;

d) digitizing the analog pulse contour;

e) analyzing the digitized pulse contour for stable waveforms;

f) processing the stable waveforms of the digitized pulse contour using dynamic time warping;

g) storing the stable waveform in a database; and h) repeating steps (a)-(g) until a suitable database has been generated.

The known arterial disease may be for example but by no means limited to congestive card iomyopathy, obliterative cardiomyopathy, asynchronous atrioventricular sequential pacing, coronary disease, hypertrophic cardiomyopathy, congestive heart failure, arteriosclerosis and cardiac insufficiency.

DESCRIPTION OF THE PREFERRED EMBODIMENTS

Figure 1:
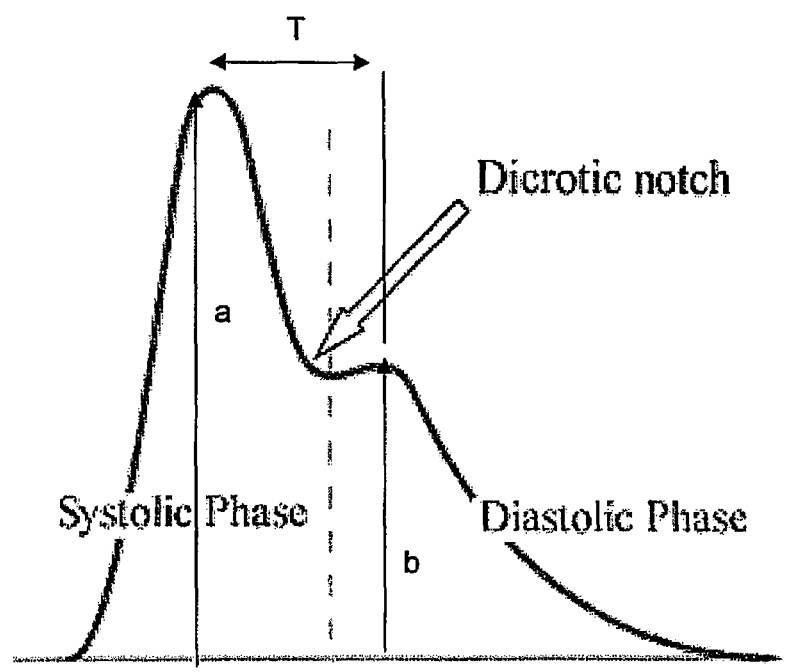
FIG. 1 shows a PPG pulse contour that is measured at a fingertip location. The front portion of the wave is called the systolic phase, the diastolic phase is the back portion of the wave, and between the two peaks is the dichrotic notch. The time T between the first and second peak is an indicator of arterial health. The stiffness index (SI) is the height of the patient in meters divided by the time T in seconds from the first to the second peak. The reflection index RI is the ratio of the smaller to larger peak height expressed in percentage terms. The peak heights can be measured in sample sizes, voltages, or another other appropriate measure because the ratio renders the specific units unimportant.
Figure 2:
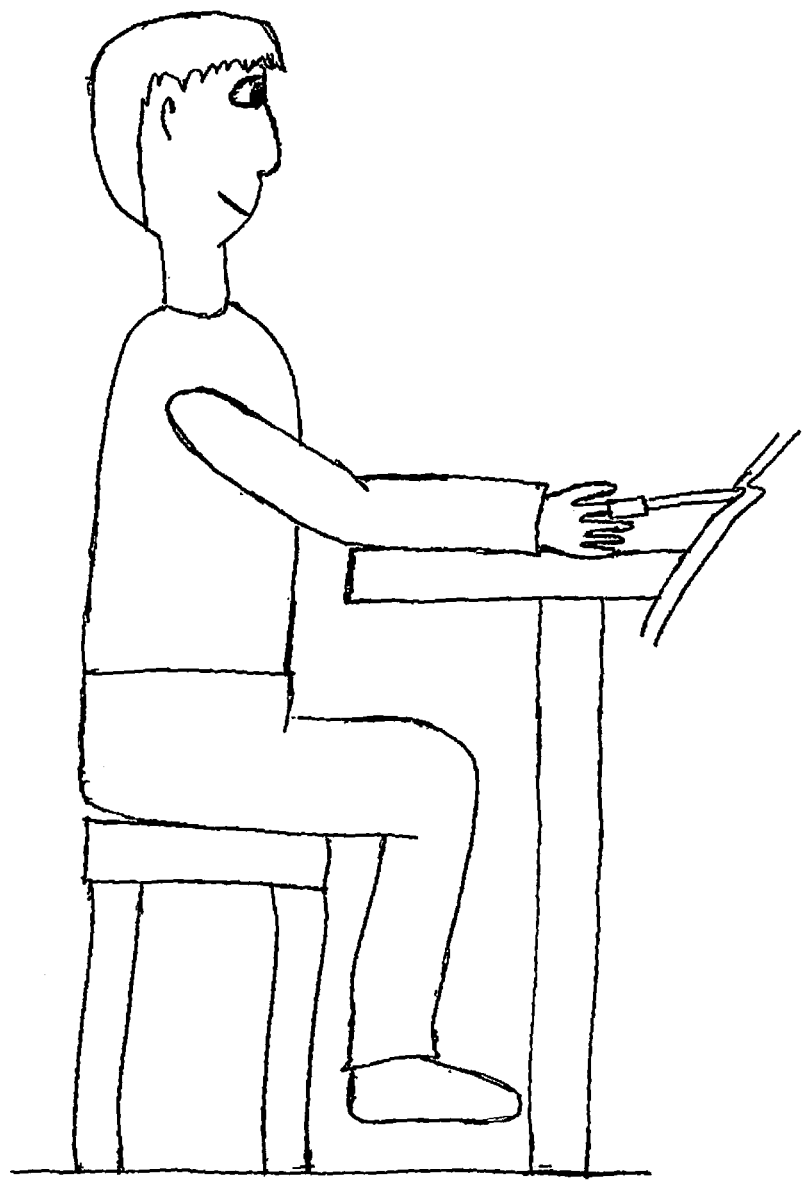
FIG. 2 shows an individual with one arm positioned so that the arm is at approximately the same height as the heart of the individual with a fingertip photoplethysmography device attached to a fingertip on the hand of the individual.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

Described herein is a method of assessing the arterial health of an individual, for example, a patient. As will be appreciated by one of skill in the art, the individual or patient may be an individual who is at risk of developing an arterial disease or may be an individual who is undergoing a check-up or other routine medical examination for determining overall health or more specifically overall arterial health of the individual.

The arterial disease may be for example but by no means limited to congestive card iomyopathy, obliterative cardiomyopathy, asynchronous atrioventricular sequential pacing, coronary disease, hypertrophic cardiomyopathy, congestive heart failure, arteriosclerosis and cardiac insufficiency.

In a preferred embodiment, a method of assessing the arterial health of an individual comprises:

a) positioning one arm of the patient such that the arm is at approximately the same height as the heart of the individual;

b) attaching a fingertip photoplethysmography device to a fingertip of the hand of said arm of the individual;

c) measuring the analog pulse contour of the individual using the fingertip photoplethysmography device;

d) digitizing the analog pulse contour;

e) analyzing the digitized pulse contour for stable waveforms;

f) processing the stable waveforms of the digitized pulse contour using dynamic time warping;

g) comparing the stable waveforms to a library of known disease state waveforms; and h) assigning a most probable disease state for the individual based on said comparison.

In some embodiments, the stable waveforms in step (e) are identified by analyzing the digitized pulse contour for two consecutive pulse heights that are within 10% of the same value.

Once a stable region has been identified, the next five wave forms are measured and stored for further processing, that is, are the stable waveforms.

As discussed below, in some embodiments, the shape of the wave and the waveform of the stable waveform are used in the assignment of the individual to a particular disease state.

In some embodiments, following step (e), the stiffness index is calculated, as discussed below.

In some embodiments, following step (e), the reflection index is calculated, as discussed below.

In a preferred embodiment, a method of generating a library of waveforms from individuals having a known arterial disease comprises:

a) positioning one arm of an individual having a known arterial disease such that the arm is at approximately the same height as the heart of the individual;

b) attaching a fingertip photoplethysmography device to a fingertip of the hand of said arm of the individual;

c) measuring the analog pulse contour of the individual using the fingertip photoplethysmography device;

d) digitizing the analog pulse contour;

e) analyzing the digitized pulse contour for stable waveforms;

f) processing the stable waveforms of the digitized pulse contour using dynamic time warping;

g) storing the stable waveform in a database; and h) repeating steps (a)-(g) until a suitable database has been generated.

The known arterial disease may be for example but by no means limited to congestive cardiomyopathy, obliterative cardiomyopathy, asynchronous atrioventricular sequential pacing, coronary disease, hypertrophic cardiomyopathy, congestive heart failure, arteriosclerosis and cardiac insufficiency. As will be appreciated by one of skill in the art, the process may be repeated until a suitable number of waveforms have been collected. Alternatively, as discussed below, the database may be updated on a continuous basis as new individuals are assessed.

As will be appreciated by one of skill in the art, in step (g), the waveform will be stored in the database such that this waveform is identified as being an example of a waveform from said known arterial disease.

In some embodiments, the stable waveforms in step (e) are identified by analyzing the digitized pulse contour for two consecutive pulse heights that are within 10% of the same value.

Once a stable region has been identified, the next five wave forms are measured and stored for further processing, that is, are the stable waveforms.

As discussed below, in some embodiments, the shape of the wave and the waveform of the stable waveform are used in the assignment of the individual to a particular disease state.

In some embodiments, following step (e), the stiffness index is calculated, as discussed below.

In some embodiments, following step (e), the reflection index is calculated, as discussed below.

As will be appreciated by one of skill in the art, including more detail on the exact condition of the individuals used to generate the database will provide a more accurate and/or informative database. Such information may include the SI and RI of the individual as discussed above as well as for example but by no means limited to their age, general health, height, weight, and other factors known about their specific arterial disease.

As discussed above, FIG. 1 shows a PPG pulse contour that is measured at a fingertip location. The front portion of the wave is called the systolic phase, the diastolic phase is the back portion of the wave, and between the two peaks is the dichrotic notch. The time T between the first and second peak is an indicator of arterial health. The stiffness index (SI) is the height of the patient in meters divided by the time T in seconds from the first to the second peak. The reflection index RI is the ratio of the smaller to larger peak height expressed in percentage terms. The peak heights can be measured in sample sizes, voltages, or another other appropriate measure because the ratio renders the specific units unimportant.

Typical values for SI for healthy younger adults will be 4 to 6, however, as we age, the SI values increase towards 10 or above. Higher values of SI are an indicator of reduced arterial health.

As discussed herein, the following functions are performed:
the height of the patient is measured in meters;
the patient sits in a comfortable position with the arm resting comfortably at near heart height;
the fingertip PPG system is attached to the patient using existing finger tip pulse measurement clips;
the analog pulse contour is measured using PPG based on known methods;
the analog pulse contour signal is digitized at a rate of 200 samples per second with an 8 bit ADC, and transmitted to a laptop or similar digital processing device;
the digitized signals are stored within a computer or memory device;
the digitized signals are monitored to search for stable waveforms, with stability being measured as a train of at least two pulse heights that are within 10% of the same value; and
after stability is found, the next five waveforms are measured and stored.

On the basis of these five waveforms, various calculations can be done. First, to calculate the patient stiffness index (SI), the SI for each of the five stable waveforms are calculated and the average of these five SI values is the calculated. In those cases where the second maxima is hard to find, a first or second derivative of the pulse contour may be taken to obtain a value for the time of the second maximum, as has been discussed in the literature.

Secondly, a reflection index (RI) may be calculated as the ratio of the height of the smaller peak divided by the height of the larger peak, to obtain a reading between 0 and 1. A first and second derivative may be required for this measurement as well. In this approach, the five stable waveforms are used, the RI of each waveform is calculated, and then the average of the five measurements is taken to obtain an average RI. The average RI can be multiplied by 100% to give a percentage value if this is desired.

Notice that this method of calculating the SI and RI is conservative, in that the best value of the SI and RI is not used, but instead an average value is used. This use of the average value will ensure that the numbers presented to the user of the program will not provide false assurance for the quality of the arterial system of the patient.

Thirdly, to calculate the most probable disease state, the five stable waveforms are: processed using dynamic time warping (DTW), are compared to a DTW library of disease state waveforms, and the most probable disease state for the patient is then presented on-screen to the user.

In order to perform the above, a library of patterns is required, with each pulse contour within this library undergoing DTW processing in order to generate a suitable DTW library curve. These library patterns are DTW versions of the various disease state curves.

The specific DTW transform that is performed is believed to be novel. For example, if the DTW processing puts additional weight on the leading edge of the pulse contour, then cardiac issues are highlighted. However, if the DTW processing puts additional weight on the trailing portion (everything after the first peak) of the curve, then arterial issues are highlighted.

Various system designs can implement this method of assessing a patient's arterial health. A first system example would use only a laptop computer, and would house the disease library on the laptop. A fingerclip would be attached to the patient, an analog to digital converter would convert the analog waveforms of the fingerclip to a digital bitstream, and the analog to digital converter would be connected to the USB port of the laptop.

This type of system is very portable, and does not require Internet or network connectivity in order to be used. In these embodiments, the pattern library is stored in the laptop as the user travels to various patient locations. The processing system on the laptop converts the patient curves to DTW versions as per the above algorithm, and the comparison is carried out on the laptop. In this arrangement, many patients can be serviced during the day in remote locations or in non-connected locations. This system may be the fastest and easiest to use, because the user and patient do not have to wait for connectivity.

A further type of application for this system is with insurance companies and travelling agents that are measuring potential client arterial health. In these embodiments, in the case where an agent works for several different insurance companies, and if the insurance companies have different versions of the disease library, then the agent needs to specify the insurance company and disease library that is being used for the comparison.

The finger clip and ADC function are standards functions known in the art. In the case of the current product, 200 Hz sampling using an 8 bit ADC is used, however many other variants and processing methods that are known in the art can be used. Increased accuracies can be achieved by using more bits for the ADC sampling method and by taking more samples per second and by using a more stable reference clock for the timing or a more stable voltage reference for the ADC system.

The laptop is commercially available and requires a USB port and sufficient processing power and memory. The disease library and processing method are believed to be novel.

The system can be designed to provide the patient or user with results information such as:
the Stiffness Index (SI) and disease state
the disease state and the RI,
the SI, disease state and RI, or
the SI and RI.

In some embodiments, the actual patient pulse contours and DTW information may be presented on the screen.

The details of one possible system are discussed below for illustrative purposes. In the following example, there is a disease library that has four disease state characteristic curves in DTW format.

As discussed above, the pulse contours are monitored until a stable pattern is found. Two successive patterns are termed stable when the maximum height that they attain is within 10%.

The first stable waveform and the next 4 waveforms are measured and averaged within this unit. The time that is used for the SI calculation is the time between the two maximum values of the curve. If there is any problem finding the location of the second maximum, then the derivative of the pulse contour is taken and the time of the second maximum is found from this first derivative curve. The height of the patient is taken in units of meters, and the time is measured in seconds. The time is calculated as the number of samples between the two maximum points, multiplied by the sampling interval time which as ¹⁄₂₀₀=5 msec. A typical value will be 2 meters divided by 0.3 seconds to give a value of 6.2 for the stiffness index.

The five waveforms after stability has been achieved are input and each has DTW conversion done to it. The output is five patient DTW waveforms. In this algorithm, library pattern 1 is used and is compared to each of the five patient DTW waveforms. The result is five distance numbers. The five distance numbers between each DTW disease state waveform and the patient waveform are input, summed and divided by 5. As previously noted, this approach for finding the distance from a given disease state will be conservative, in that the closest fit is not selected, but instead the average fit is selected. The result is the average distance from the first disease state.

The above two measurements and calculations are repeated for library patterns 2, 3, and 4. The averages are found, and therefore 4 average numbers emerge, which are the distances from the four library disease states to the patient state.

The smallest distance number indicates the closest patient DTW pattern to disease state pattern. If the smallest number comes from average 1, then library pattern 1 is the closest disease state which means that a certain disease trend may be evident for this patient. This information is presented to the user and/or patient.

As discussed above, in this illustrative example, four library patterns indicate four basic disease states.
Class I: a distinct incisura is inscribed on the downward slope of the pulse wave
Very sharp wave, the waveform covers small area: acute anteroapical myocardial infarction
Round waveform, long diastolic top: congestive cardiomyopathy
Disordered waveform: obliterative cardiomyopathy
Large slope and round wave top: asynchronous atrioventricular sequential pacing
Class II: No incisura develops but the line of descent becomes horizontal
Weak wave, slow change: coronary disease
Round waveform: hypertrophic cardiomyopathy
Round wave top and slow change rate at diastolic component: congestive heart failure
Class III: No notch is present but a well-defined change in the angle of descent is observed
Regular wave: arteriosclerosis
Round waveform: hypertrophic cardiomyopathy
Class IV: No evidence of a notch is seen
Sharp wave: cardiac insufficiency
Regular wave: arteriosclerosis All waveform patterns are stored under those four classes. A DTW calculation between testing data and class samples is used to determine the class of the testing data. Then calculations between testing data and all samples within the class are performed to find the best matching sample. We use the description and medical record of the matching sample as reference to the testing data.

Library Reference data for these disease states has been obtained from previous publications, which are:
1. Dawber T R, Thomas H E, McNamara P M. Characteristic of the dicrotic notch of the arterial pulse wave in coronary heart disease. Angiology. 1973; 24:244-255
2. He S Y, Liu S B, Diagnostics of Clinic Pulse Wave. People's Military Medical Press. 2004
3. Wilmer W. Clinical Measurement of Arterial Stiffness Obtained From Noninvasive Pressure Waveforms. the American Journal of Hypertension. 2004 and are incorporated herein by reference in their entirety.

As will be appreciated by one of skill in the art, these disease state descriptions are general for illustrative purposes; more detailed disease state descriptions may also be used in the library/database as desired.

As will be appreciated by one of skill in the art, additional complexity can be introduced to this system by increasing the sophistication of the stability algorithm.

As well, additional library patterns can be added over time to ensure that various disease states are being matched to the patient information.

The laptop may be exchanged for a smaller portable device, or could be a watch or personal computing system.

The ADC and fingertip device could be integrated together into a single package.

In some embodiments, the DTW algorithm itself can have various weightings of the various points of the distance measurement, and more complicated distance measurement could be done.

As will be appreciated by one of skill in the art, none of these improvements modify the basic design of construction of the system.

Additional system designs are also contemplated. The system above is a simple system that does not use network or internet connectivity to enhance performance. One embodiment of the system uses on-board processing and an on-board library and is capable of providing real-time and local results. Alternative system architectures that perform the same basic functions in other ways will be readily apparent to one of skill in the art.

For example, the system can be improved and modified to allow changes in for example billing, security, disease library control, and to modify the processing requirements of the equipment connected to the fingerclip.

For instance, imagine that an insurance company has many agents in the field which are using the PPG system for assessing patient status. Instead of having the disease library in the laptop, the insurance vendor wishes to have the disease library centralized for security and performance reasons. In this system, the library of patterns exists in the insurance company site, and the internet is used as the connection method. The library can be updated easily because it is centralized. In this example, the laptop would send the average patient waveform to the library, either before or after DTW processing depending on the details of the system design, the level of connectivity which is available, and the cost of the connective, and the library would send back a response with the information to be presented to the customer.

This approach is useful when the customer wishes to have increased control of the pattern library for easy updating and control. In this case, if different life insurance companies have different libraries that they wish to use for their particular disease state identifiers, then each insurance company can have control of their own library. This approach is also useful if each patient pulse contour history is maintained by a customer, in which case a centralized location may allow the most effective security of the patient record in accordance with the government policies on health records that may exist in different locales and nations.

In another system example, a vendor may be located between the insurance company and the laptop. This is useful if a vendor wishes to have increased control of the amount of measurements being done, either for security or transaction processing reasons. This system is most effective if a vendor is providing the measurements to the patient, and the insurance company is being served with the vendor information. As shown here the insurance company would still have control of the patient record, and the database at vendor would contain billing and transaction information. The disease library can be updated easily because it is centralized, and it is still in control of the insurance company. In this example, the laptop would send the average waveform to the insurance company via the vendor. This system design may be useful if the insurance agents using the laptop are part of the vendor business, but are using disease libraries from one or more insurance companies.

An alternative system design is one in which both insurance company site and vendor site are contacted by the laptop unit via the internet or network medium. In this system, the vendor site does not limit the processing speed of the insurance company site.

For each of these various system types, the basic functions performed by the system are the same.

While the preferred embodiments of the invention have been described above, it will be recognized and understood that various modifications may be made therein, and the appended claims are intended to cover all such modifications which may fall within the spirit and scope of the invention.

The invention claimed is:

1. A method of assessing arterial health of an individual comprising:
   a) positioning one arm of the individual such that the arm is at the same height as a heart of the individual;
   b) attaching a fingertip photoplethysmography device to a fingertip of a hand of said arm of the individual;
   c) measuring an analog pulse contour of the individual using the fingertip photoplethysmography device;
   d) digitizing the analog pulse contour;
   e) analyzing the digitized analog pulse contour for stability by analyzing the digitized pulse contour for two consecutive pulse heights such that the second pulse height of the two consecutive pulse heights is within 10% of the first pulse height of the two consecutive pulse heights thereby finding stability, and then after stability is found, measuring and storing waveforms of the digitized analog pulse contour immediately subsequent to the two consecutive pulse heights, the subsequent waveforms being stable waveforms;
   f) processing the stable waveforms of the digitized analog pulse contour;
   g) comparing the stable waveforms to a library of known disease state waveforms; and
   h) assigning a most probable disease state for the individual based on said comparison, and presenting said most probable disease state to a user.

2. The method according to claim 1 wherein following step (e), a stiffness index is calculated.

3. The method according to claim 2 wherein each stable waveform has a wave peak and the stiffness index is height of the individual in meters divided by time in seconds between wave peaks of two adjacent stable waveforms.

4. The method according to claim 1 wherein following step (e), a reflection index is calculated.

5. The method according to claim 1 wherein the user is an insurance agent assessing the arterial health of the individual.

6. The method according to claim 1 wherein the library of known disease state waveforms comprise four library patterns indicating four basic disease states.

* * * * *